United States Patent
Muenker (10) Patent No.: US 9,322,789 B2
(45) Date of Patent: Apr. 26, 2016

(54) METHOD FOR FEEDING X-RAY FLUOROSCOPY IMAGES IN THE CONTEXT OF A DIGITAL LAMINOGRAPHY TECHNIQUE AND USE OF A MULTIAXIS MANIPULATOR SYSTEM FOR CARRYING OUT SAID METHOD

(71) Applicant: YXLON International GmbH, Hamburg (DE)

(72) Inventor: Martin Muenker, Gevelsberg (DE)

(73) Assignee: YXLON INTERNATIONAL GMBH, Hamburg (DE)

( * ) Notice: Subject to any disclaimer, the term of this patent is extended or adjusted under 35 U.S.C. 154(b) by 94 days.

(21) Appl. No.: 13/935,629

(22) Filed: Jul. 5, 2013

(65) Prior Publication Data

US 2014/0016744 A1   Jan. 16, 2014

(30) Foreign Application Priority Data

Jul. 6, 2012   (DE) .......................... 10 2012 013 500

(51) Int. Cl.
*A61B 6/00*   (2006.01)
*G01N 23/00*   (2006.01)
(Continued)

(52) U.S. Cl.
CPC ............... *G01N 23/04* (2013.01); *G01N 23/046* (2013.01); *A61B 6/025* (2013.01); *A61B 6/032* (2013.01); *G01N 2223/309* (2013.01); *G01N 2223/419* (2013.01)

(58) Field of Classification Search
CPC .................. G01N 2223/309; G01N 2223/419; G01N 23/04; G01N 23/046; A61B 6/025; A61B 6/032
See application file for complete search history.

(56) References Cited

U.S. PATENT DOCUMENTS 6,459,759 B1   10/2002   Tominaga
7,899,152 B2   3/2011   Boese et al.
(Continued)

FOREIGN PATENT DOCUMENTS

DE   102007037996 A1   2/2009

OTHER PUBLICATIONS

Vishnyakov, G.N.; Levin, G.G, : Optical tomography of living cells using phase shifting Linnik microscope. In; Proceedings SPIE 3568, Optical Biopsies and Microscopies Techniques III, 197 (Dec. 1999). pp. 197-200.

(Continued)

*Primary Examiner* — David J Makiya
*Assistant Examiner* — Dani Fox
(74) *Attorney, Agent, or Firm* — Leydig, Voit & Mayer, Ltd.

(57) ABSTRACT

A method is provided for feeding-in X-ray fluoroscopy images of an object in the context of a digital laminography technique, in which the X-ray fluoroscopy images are not fed in at 360°, but a feed-in of first X-ray fluoroscopy images takes place at 180° and, after tilting the object, a feed-in of second X-ray fluoroscopy images follows in the same angular range of 180°. The second X-ray fluoroscopy images, after suitable reflection onto the complementary points, are set to the first X-ray fluoroscopy images and, from the resultant complete data set, a calculation is carried out in the context of the digital laminography technique. A multiaxis manipulator system is used for feeding-in X-ray fluoroscopy images in the context of carrying out a digital laminography technique on an object, which is secured on a fixing device of the manipulator system.

10 Claims, 4 Drawing Sheets (51) Int. Cl.
*G01N 23/04* (2006.01)
*A61B 6/03* (2006.01)
*A61B 6/02* (2006.01)

(56) References Cited

U.S. PATENT DOCUMENTS

2005/0074088 A1* 4/2005 Ichihara et al. .................. 378/58

2009/0279662 A1* 11/2009 Rietzel ........................... 378/62

OTHER PUBLICATIONS

Maisl, M.; Computed Laminography, Basic Principles and Technical Implementation, (Sep. 2010), pp. 261-266.

* cited by examiner

METHOD FOR FEEDING X-RAY FLUOROSCOPY IMAGES IN THE CONTEXT OF A DIGITAL LAMINOGRAPHY TECHNIQUE AND USE OF A MULTIAXIS MANIPULATOR SYSTEM FOR CARRYING OUT SAID METHOD

CROSS REFERENCE TO RELATED APPLICATIONS

This application claims priority from German Patent Application No. 10 2012 013 500.9, filed Jul. 6, 2012, which is hereby incorporated by reference herein in its entirety.

FIELD

The invention relates to a method for feeding-in X-ray fluoroscopy images in the context of a digital laminography technique and to the use of a multiaxis manipulator system for feeding-in X-ray fluoroscopy images in the context of carrying out a digital laminography technique.

BACKGROUND

Digital laminography—also called tomosynthesis—is a method of generating a three-dimensional representation of an object by means of X-raying that is not free from superimposed structures. It is particularly suitable for examining primarily flat objects. In digital laminography the object is irradiated from different directions. As a rule the irradiation takes place in discrete positions, which in linear laminography are in a plane that is (approximately) perpendicular to the principal plane of the object, and in rotational laminography are on a cone whose principal axis is (approximately) perpendicular to the principal plane of the test object. A complete data set for laminography is produced by a synchronous, opposed, generally linear or circular motion of radiation source and detector, relative to a reference point generally located in the object. Imaging is characterized by the motion of the detector relative to the reference point, the motion of the radiation source relative to the reference point, the tilt angle to the central ray, the number of projections, the detector-reference point distance and the radiation source-reference point distance. It is unimportant whether this relative motion is produced by the positioning of the imaging system (radiation source and detector) around the object at rest, or by the motion of individual or several components around the object, which is also moving, or only from the motion of the object while the imaging system is stationary.

A complete laminography data set for the test zone located around the reference point is produced by rotating the object by means of a rotating unit about an axis passing through the object. The imaging system, consisting of radiation source and detector, is tilted at a defined angle to the rotation axis. The central ray meets the object exactly or approximately where the rotation axis pierces the object. The reference point is defined as the point of intersection of rotation axis and central ray. Relative to this reference point, radiation source and detector virtually perform a synchronous, opposed circular motion.

A variant of the set-up just described envisages that the imaging system is oriented horizontally; the rotation axis is, accordingly, tilted at an angle to the central ray. Radiation source and detector perform a synchronous, opposed circular motion relative to the reference point. The aforementioned boundary conditions remain valid.

A disadvantage with these arrangements is that the size of the rotating unit limits the maximum size of the test object; in particular the production of precise positioning units for large and heavy objects is expensive and they must in each case be manufactured individually. Another disadvantage is that the mechanical realization of the rotational motion essentially defines the position of the reference point; in order to change the position of the test zone, the test object must be moved within the rotating unit relative to the reference point.

However, it is desirable to be able to choose the position of the reference point freely in the whole test object. To achieve this, either the object must be arranged movably within the rotating unit, i.e. another movement unit is necessary, which must be rotated in the system, or the rotating unit must be movable in the X/Z direction, i.e. perpendicular to the rotation axis, so that the position of the eccentrically arranged reference point is moved into the rotation axis by an X/Y motion.

SUMMARY

In an embodiment, the present invention provides a method for feeding-in X-ray fluoroscopy images in the context of a digital laminography technique. The method includes securing an object to be examined on a fixing device of a multiaxis manipulator system and positioning the object using the multiaxis manipulator system so that a central ray of an X-ray fluoroscopy device including an X-ray tube and an X-ray detector passes through a reference point to be defined. The object is moved using the multiaxis manipulator system into assignable first positions, at each of which a feed-in of a first X-ray fluoroscopy image takes place. The first positions fulfill the following boundary conditions: the reference point remains essentially unchanged relative to the X-ray irradiation device, a normal through the reference point, relative to a surface of the object forms a tilt angle ($\phi$) with the central ray that is between $-45°$ and $+45°$, and the tilt angle ($\phi$) and the central ray are essentially always in the same plane in all positions, where a rotation can have taken place about the normal through a rotation angle ($\alpha$) that is between $-90°$ and $+90°$. The multiaxis manipulator system is moved to second positions, which are reflected to the first positions relative to a mirror plane that passes through the reference point and is perpendicular to the central ray. A feed-in of second X-ray fluoroscopy images takes place at these second positions. The second X-ray fluoroscopy images are reflected in the horizontal and vertical direction in an analysis unit. All of the first X-ray fluoroscopy images and the reflected second X-ray fluoroscopy images are used as a data set for calculation in the context of the digital laminography technique.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

An aspect of the present invention is to provide a method that can be achieved as flexibly and simply as possible, both with respect to the manipulator to be used and with respect to the type and size of the component to be examined and the imaging result to be achieved, wherein this should apply in particular to the volumetric visualization of small and medium-sized objects.

In an embodiment the present invention provides a method using a multiaxis manipulator system, which in particular includes industrial robots with at least four axes. In the method according to the invention it is essential that in all positions that the object assumes in the feed-in of fluoroscopic images, the central ray of the X-ray fluoroscopy device always goes through the same reference point, as it is around this reference point that the object is examined by means of the laminography technique according to the invention. Because the method according to the invention is carried out by means of a multiaxis manipulator system it is not necessary, as is known from the state of the art, to use manipulator systems that are so large that the object to be tested is enveloped by them completely and a complicated mechanism must be provided to allow the object to be moved to a position in which the reference point—and thus the zone that is to be examined by the laminography technique—is moved to the place where the central ray passes through the object. Owing to the variable tilt angle, which is between −45° and +45°, and because the tilt angle and the central ray in all positions always lie in the same plane and rotation can take place about the normal through a rotation angle between −90° and +90°, the method according to the invention offers a large number of different possibilities for establishing the positions at which the fluoroscopic images are fed in. This gives it the flexibility that various types of laminography techniques can be carried out, in particular laminography techniques on free paths of motion, elliptical laminography techniques, rotational laminography techniques, but also linear laminography techniques. To establish the first positions for feed-in of the fluoroscopic images, only one half of the fluoroscopic images required for laminography are fed in, which for example are located below the reference point. Contrary to the state of the art, the object is not then rotated further, in order to feed in fluoroscopic images in the second positions located above the reference point. Rather, for controlling these second positions, the first positions are reflected onto the mirror plane, which passes through the reference point and is perpendicular to the central ray. Together with the corresponding reflection of the second fluoroscopic images fed-in in these second positions in the horizontal and vertical direction, this is equivalent to the previously described rotation of the object through more than 180°. As a result it is possible for the manipulator system to be configured more simply and the problem that in some positions (whether the first or the second positions) part of the manipulator system would lie in the beam path of the X-ray fluoroscopy device, is avoided. For calculation in the context of the digital laminography technique, with the non-reflected fluoroscopic images from the first positions and the reflected fluoroscopic images from the second positions, as described above, a complete data set is available, corresponding to the laminography technique known from the state of the art.

An advantageous variant of the invention envisages that the tilt angle is related to the rotation angle as follows:

$$\phi(\alpha) = \phi_0 - 2a^*(1-\cos(\alpha - \alpha_0)),$$

where $\phi_0$ is an assignable maximum tilt angle from the range [−45°; +45°], which predetermines the major axis in elliptical laminography, and $\alpha_0$ is an assignable torsional angle from the range [−90°; +90°], which predetermines the torsion of the major axis in elliptical laminography relative to the horizontal, and "a" is a measure for the eccentricity of the ellipse from the range [0°; $\phi_0/2$]. Based on this relation, an elliptical laminography technique can be carried out in which the major axis of the ellipse is twisted through an assignable constant torsional angle relative to the horizontal. From the pattern of motion in the known laminography techniques, the number of fluoroscopic images fed in and the distances between X-ray tube and reference point and reference point and detector—from which in its turn the geometric enlargement is obtained—the achievable detail discrimination is determined in conjunction with the inherent properties of the imaging system. From the number and distribution of the first positions in the method according to the invention, a preferred direction is derived for the detail discrimination in the test zone, wherein the tilt angle predetermines the achievable depth resolution in the direction of the rotation axis. By twisting the major axis of the ellipse, it is possible to determine in what direction the resolution around the reference point should be particularly high or particularly low.

Another advantageous variant of the elliptical laminography technique just described is obtained when the constant torsional angle is set at $\alpha_0 = 0°$ or 90°. This simplifies the relation given above between the rotation angle and the tilt angle, and the major axis of the ellipse coincides with the horizontal or with the vertical.

If, in a method of an embodiment of the invention, the tilt angle is kept constant, a circular relative motion can be produced—corresponding to rotational laminography. This is particularly preferable when a detail discrimination that is isotropic around the reference point is to be achieved for all viewing directions.

An even simpler laminography technique is obtained when the rotation angle α is kept constant and a rotation is performed in the direction of the tilt angle φ, or when the tilt angle φ is kept constant and a rotation is performed in the direction of the rotation angle α. In both cases the pattern of motion of linear laminography is obtained, in which details oriented in the direction of motion can only be represented to a limited extent. For applications in which this is sufficient, linear laminography is preferred owing to its simple path of motion between the first or second positions. The multiaxis manipulator, in particular an industrial robot, allows free orientation of the direction of motion relative to the central ray.

Another advantageous variant of the invention envisages that the rotation angle in one of the first positions is −90° and in another of the first positions is +90°. This gives a laminography technique in which, in particular, fluoroscopic images are also fed-in in the extreme positions and therefore good resolution is also achieved in these places. This applies in particular with respect to the advantageous variant of the method according to the invention in which the first positions during feed-in of the first X-ray fluoroscopy images have equal rotation angle distances from one another, in particular, adjacent first positions are twisted relative to one another through a rotation angle α=10°. As a result of this small-angle division of the fluoroscopic images, a very good resolution is achieved over the whole 360°.

Another advantageous variant of the invention envisages that none of the parts of the multiaxis manipulator system is located, either in the first positions or in the second positions, in the beam path of the X-ray fluoroscopy device. This has the result that in none of the first and second positions is there a loss of detail discrimination owing to a partially shadowed fed-in fluoroscopic image, as a part of the manipulator system would be located in the beam path. In contrast to the manipulators known from the state of the art, with the multiaxis manipulator system used in the method according to the invention this can also be achieved very simply. Even during a movement from one position to the next position, in which in each case fluoroscopic images are fed in, with the multiaxis manipulator system it is possible that none of its parts is located in the beam path.

In an embodiment, the present invention also provides the use of a multiaxis manipulator system for feeding-in X-ray fluoroscopy images in the context of carrying out a digital laminography technique on an object to be examined, which is secured on a fixing device of the manipulator system. As already explained above, owing to the multiaxis manipulator system it is possible without any problem to go to all required first and second positions in which fluoroscopic images are fed in, so that at little cost, no parts of the manipulator system are located in the beam path. The use according to the invention preferably takes place during carrying out of a method according to the invention.

Figure 1:
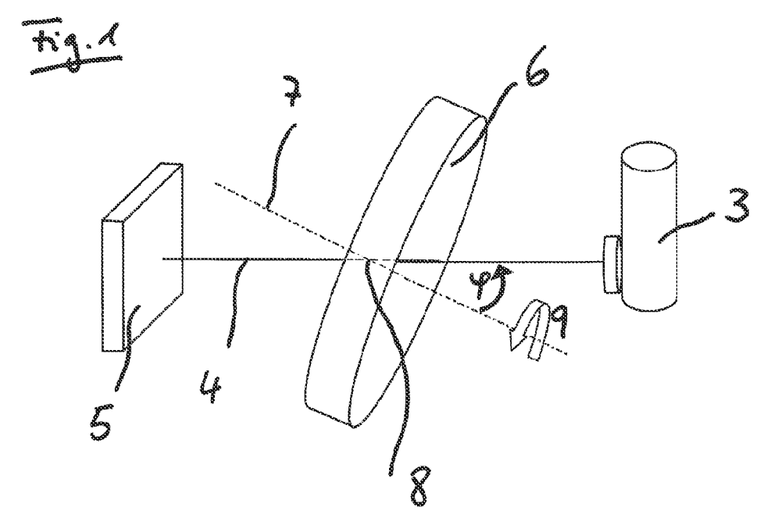
FIG. 1 shows a simplified perspective view of a system for carrying out conventional rotational laminography.

FIG. 1 is a schematic perspective view of an X-ray fluoroscopy device, with an object 6 for examination arranged in its beam path. The X-ray fluoroscopy device has an X-ray tube 3, the central ray 4 of which impinges essentially normally on an X-ray detector 5.

It is most sensible to use laminography techniques when a primarily flat object 6 is to be examined. The region around the point at which the central ray 4 passes through the object shown 6 is investigated. This point is designated hereinafter as the reference point 8. In FIG. 1, the object 6 is oriented so that its normal 7 with respect to the surface at the reference point 8 is tilted at a tilt angle φ relative to the central ray 4.

Figure 4:
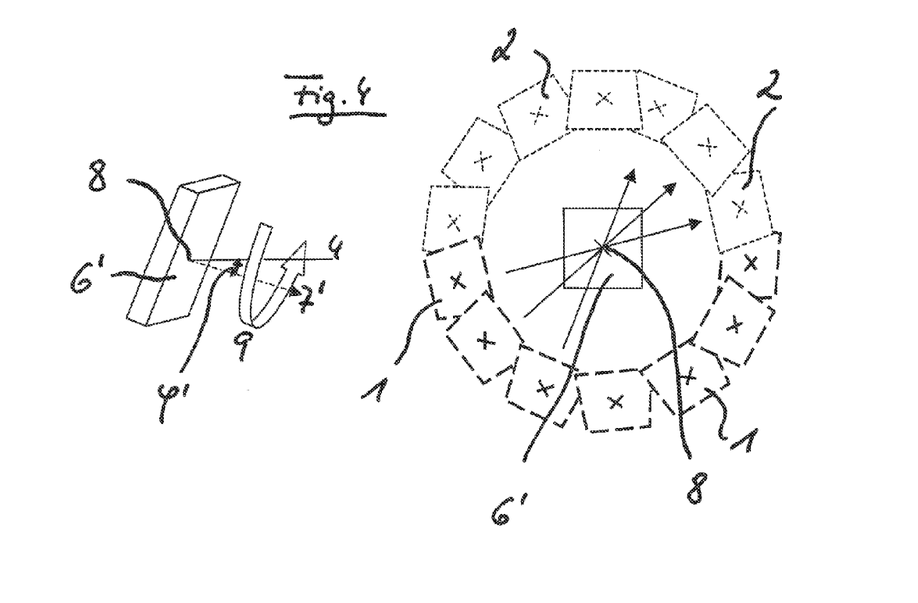
FIG. 4 shows a view as in FIG. 2, but during the feed-in of second X-ray fluoroscopy images and view of the arrangement both of the first and of the second X-ray fluoroscopy images.
Figure 5:
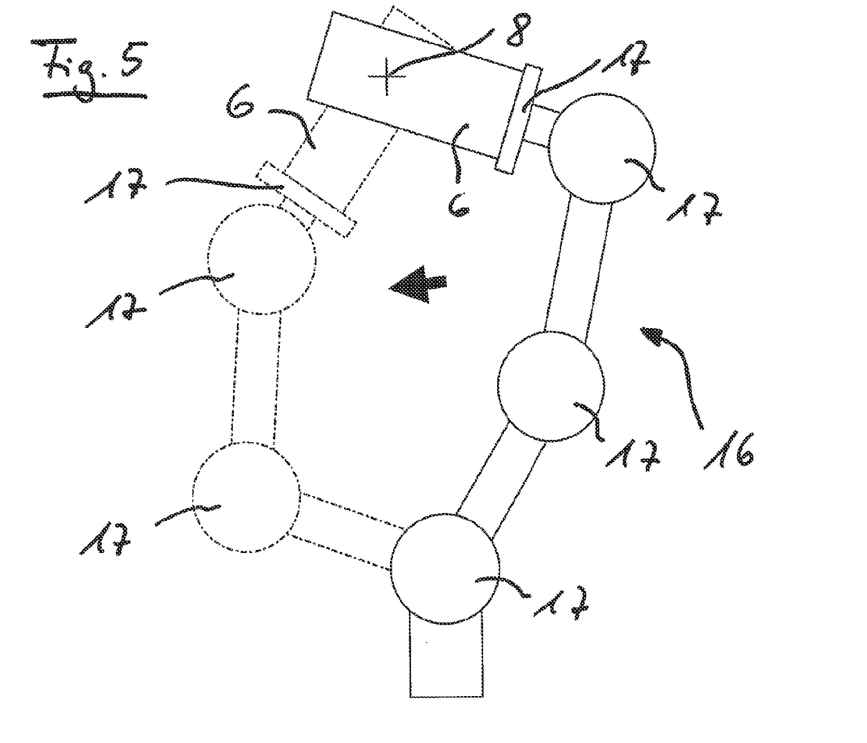
FIG. 5 shows a schematic representation of the pattern of motion of a robot when carrying out elliptical laminography.

The object 6 is held in the position shown by a manipulator system 16 (see FIG. 5). According to the invention, any multiaxis manipulator system 16 that has at least four movable manipulator axes 17 can be considered as the manipulator system 16. This can involve the large and expensive linear manipulators known from the state of the art, in which the object 6 is clamped. However, an industrial robot, which grasps the object 6 definitively with its gripper, is preferred and is more suitable for the method according to the invention, particularly with respect to the rotational laminography shown in FIGS. 1-4. As a person skilled in the art knows how an industrial robot reliably grasps an object, in particular the object 6, and holds it in position—as shown in FIG. 1, this will not be described in more detail here.

As the use of an industrial robot is particularly advantageous for carrying out the invention, just one embodiment of a manipulator system 16 in this form will be described in the following.

In the rotational laminography techniques employed until now, a rotation 9 of the object 6 about the normal 7 takes place and at predetermined rotation angles about the normal 7 (in FIG. 6b, which relates to rotational laminography, this has been given the reference symbol α), X-ray fluoroscopy images 1, 2 of the reference point 8 and its surroundings are fed in. This takes place over a full rotation through 360°. The X-ray fluoroscopy images then fed-in, distributed over 360°, are processed by means of an algorithm known by a person skilled in the art, for reconstruction of the object 6 in the region around the reference point 8.

In rotational laminography, the depth resolution is isotropic in all spatial directions, as the tilt angle φ is kept constant. It is different in the other laminography techniques, which are described below in FIGS. 6a, 6c and 6d. The imaging parameters include not only the tilt angle φ, but also the enlargement that is produced owing to the distance from the reference point 8 to the X-ray tube 3 and to the X-ray detector 5.

With the control systems of industrial robots there is no problem in executing movements of the object 6 in such a way that the reference point 8 does not change its position in space. This applies at least to the positions in which X-ray fluoroscopy images 1, 2 (see FIGS. 2 and 4) are fed in. For the invention it is not important how the industrial robot moves and what positions the reference point 8 assumes between two positions at which X-ray fluoroscopy images 1, 2 are fed in. It is only decisive that at these feed-in positions both the reference point 8 spatially, and the tilt angle φ always remain unchanged.

The method according to the invention does not, however, rotate through the full 360° with the tilt angle φ unchanged. With an industrial robot this would only be possible with complex movements and with massive restrictions of the range of movement, as otherwise at any angular range of the 360° about the normal 7, in all cases a part of the industrial robot would be in the beam path, so that in these places no X-ray fluoroscopy images 1, 2 could be fed in that did not contain defects. However, it is possible without any problem to have an industrial robot execute a rotation of the object 6 through 180° about the normal 7, without parts of it getting in the beam path.

Figures 2, 3:
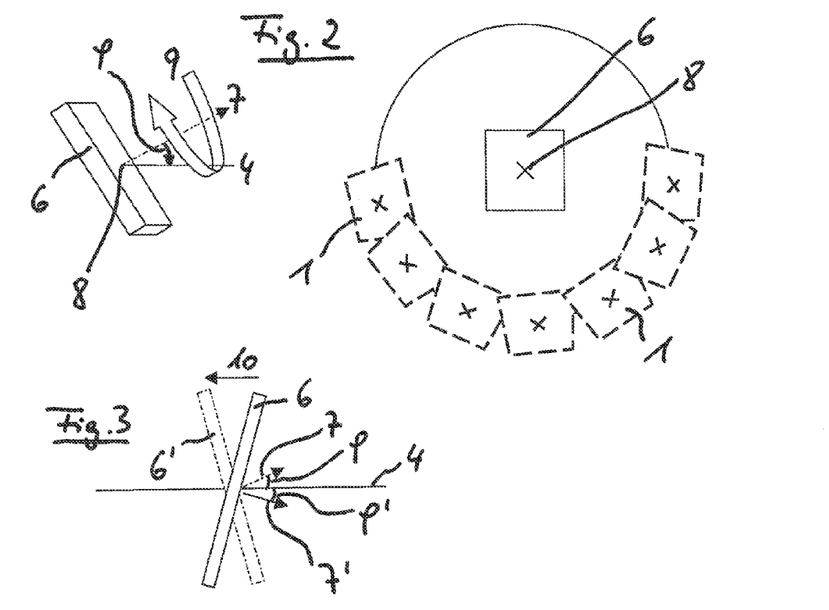
FIG. 2 shows a schematic representation of a part of the system according to FIG. 1 for obtaining first X-ray fluoroscopy images and the arrangement of these X-ray fluoroscopy images.
FIG. 3 shows a schematic representation of the transition from the feed-in of the first X-ray fluoroscopy images to the feed-in of the second X-ray fluoroscopy images.

According to the invention, with this industrial robot, which is used for carrying out rotational laminography, the procedure according to FIGS. 2-4 is therefore followed.

The starting point according to FIG. 2 is identical to the spatial orientation shown in FIG. 1. During the rotation 9 of the object 6 through 180° viewed in the clockwise direction from the X-ray tube 3 about the normal 7, which includes a fixed tilt angle φ relative to the central ray 4, at least in the positions in which the first X-ray fluoroscopy images 1 are fed in, the reference point 8 remains in the same place. According to the right-hand part of FIG. 2, at a total of seven positions a first X-ray fluoroscopy image 1 is fed in. Any other number of first X-ray fluoroscopy images 1 fed-in is equally possible; it is advantageous, for example, to feed in a first X-ray fluoroscopy image 1 every 10°, so that eighteen of these first X-ray fluoroscopy images 1 would be produced. The fed-in images are in each case a distorted image of the part of the object 6 shown centrally in the right-hand part of FIG. 2 about the reference point 8 marked with a cross. The respective distortion at the seven positions is known owing to the geometric parameters—the enlargement owing to the distance from the reference point 8 to the X-ray tube 3 and to the X-ray detector 5, the tilt angle φ and the angles with respect to the rotation 9 about the normal 7—as in a method according to the state of the art, or it can be calculated. Therefore a reconstruction can take place using the known algorithms.

After a rotation 9 through 180° about the normal 7, with feed-in of the seven first X-ray fluoroscopy images 1, has taken place in this example—this is indicated in FIG. 3 with solid lines for the object 6, the normal 7 and the tilt angle φ—a mirror movement 10 is executed. The object 6 is brought into a new position, which is shown with dashed lines and is marked 6'. According to the invention, this is a reflection relative to a mirror plane, which passes through the reference point 8 and is perpendicular to the central ray 4. This results in a tilting of the object 6, so that its normal 7 moves to its new position, marked 7', along the mirror movement 10, wherein the normal 7, 7' and the central ray 4 lie in one plane, wherein in addition the angle between the central ray 4 and the normal 7' in the new position of the object 6'—which is marked with φ'—as regards its value, corresponds to the tilt angle φ. Therefore, as the end result there is tilting by twice the tilt angle φ in FIG. 3 upwards (thus anticlockwise).

FIG. 4 shows the object 6' in its new position with the new orientation of the normal 7' and the new tilt angle φ' relative to the central ray 4 with the reference point 8 unchanged.

Starting from this orientation, there is rotation 9 once again through 180° about the now newly oriented normal 7; but this time in the opposite direction, as described above referring to FIG. 2. Once again, seven second X-ray fluoroscopy images 2 are fed in at seven positions, which are reflected to the first positions relative to the mirror plane.

The second X-ray fluoroscopy images 2 that are fed-in are reflected in the horizontal and vertical direction, as shown in the right-hand half of FIG. 4. This then corresponds to the conventional turning of the object 6 through 360°. In an analysis unit (not shown), a reconstruction of the object 6 around the reference point 8 with isotropic depth resolution in all viewing directions, is then calculated on the basis of the available fourteen X-ray fluoroscopy images 1, 2 (wherein the second X-ray fluoroscopy images 2, as described above, were reflected) by means of a known algorithm, which is also used in the state of the art.

Basically, the order in which the individual positions 1 and 2 are approached is unimportant, provided the assignment of the projection images to the positions is retained.

As the industrial robot, in the method according to the invention carried out according to FIGS. 2-4 above, does not have to execute a rotation of the object 6 through 360°, but only through 180° followed by a backward motion again through 180° (see FIGS. 2 and 4), it is ensured over the entire travel that no parts of the industrial robot get in the beam path, which would lead to unusable X-ray fluoroscopy images 1, 2.

In the method according to the invention for carrying out rotational laminography it is therefore possible to use a commercially available industrial robot instead of a multiaxis positioning system tailored individually to the testpiece with respect to size and weight. By varying the position of the test zone of the object 6 within the reach of the industrial robot with the intuitively accessible parameters tilt angle φ, rotation angle α, reference point 8 and radius and the distances from the object 6 to the X-ray tube 3 and to the X-ray detector 5 relative to the reference point 8, which are relevant for establishing the enlargement, the resolution and the size of the test zone, an extremely advantageous implementation of the rotational laminography technique is achieved. By means of the tilt angle φ, it is possible to optimize the depth resolution very simply and over extensive stretches.

As the method can be carried out with conventional industrial robots, it is in particular also suitable for retrofitting existing robot-based radiography equipment. The imaging system is fixed during testing, so that there are no requirements on type and extent of motion of the imaging system. Within the motion and loading range of the industrial robot, the size of the object 6 and test zone around the reference point 8 can be defined entirely freely. Imaging quality correlates with the positioning accuracy of the industrial robot. Movement, enlargement and tilt angle φ can be freely chosen within the limits of the system. Detail discrimination and size of the test zone can therefore be varied over a wide range.

The above advantages are also achieved with respect to the other laminography techniques. The differences of the common laminography techniques are shown in FIGS. 6a-6d and are described below.

Figure 6A:
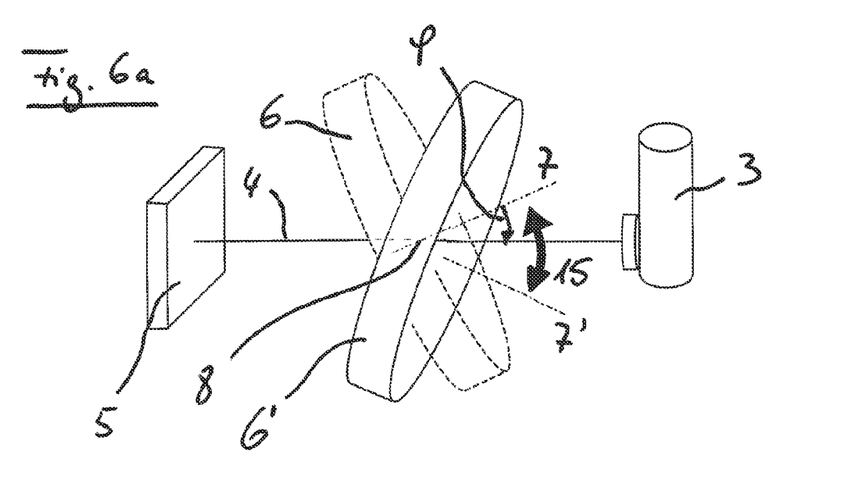
FIG. 6a shows a schematic representation for explaining the execution of linear laminography.

Linear laminography is explained on the basis of FIG. 6a. In linear laminography, the tilt angle is varied. The rotational motion takes place about a (virtual) rotation axis, which is perpendicular to the central ray, but otherwise can have any orientation. Depending on the gripping direction, this can be achieved with the most varied patterns of motion of the multiaxis manipulator. Normally this movement is not critical with respect to shadowing, therefore does not require splitting of the projection series and therefore is not a subject of the invention; the explanation only serves for completeness, as it represents an extreme form of elliptical laminography.

In FIG. 6b, once again rotational laminography is considered, wherein the projection shown is depicted perpendicular to the normal 7 (see FIGS. 1-4) that passes through the reference point 8 at the mid-point of the circular path 12. This figure shows the rotation angle, through which the object 6 (not shown in FIG. 6b) is moved about the normal 7 owing to the rotation 9 (see FIGS. 2 and 4).

Figure 6B:
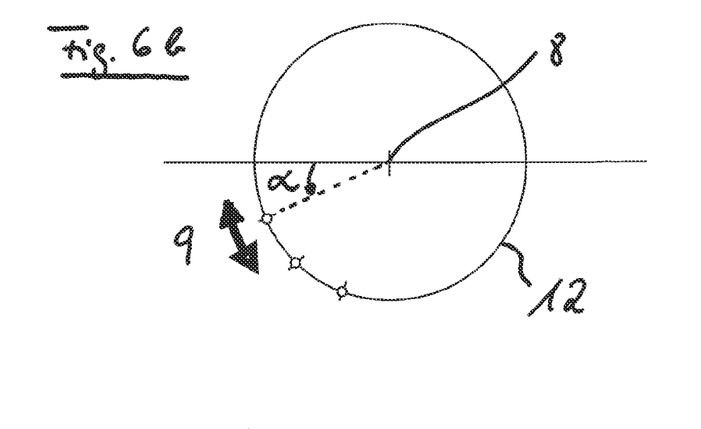
FIG. 6b shows a schematic representation for explaining the execution of rotational laminography.
Figure 6C:
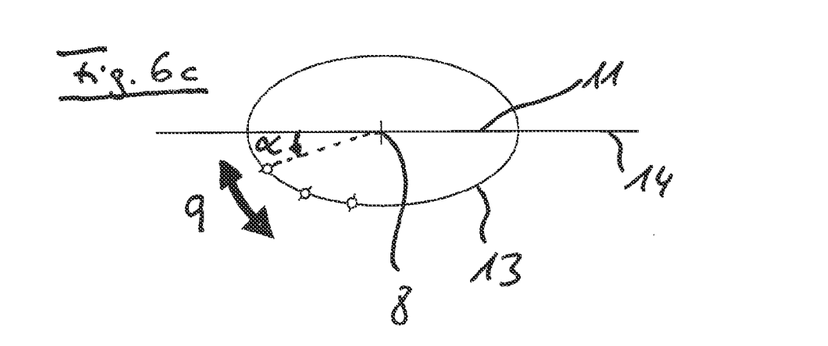
FIG. 6c shows a schematic representation for explaining the execution of elliptical laminography and FIG. 6d shows another sketch for explaining the execution of elliptical laminography, but with the major axis twisted relative to the horizontal.
Figure 6D:
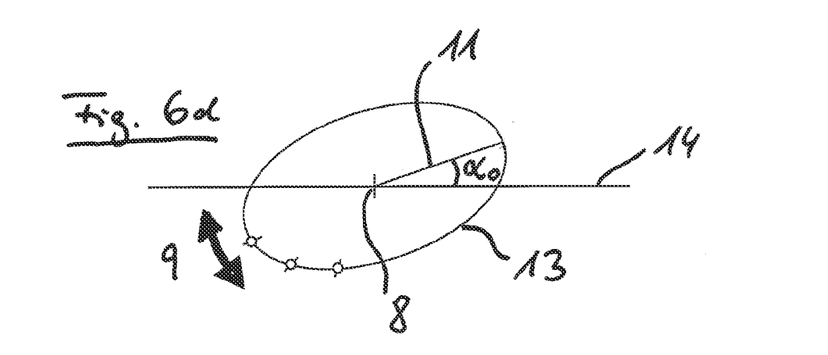

FIGS. 6c and 6d show two different embodiments of elliptical laminography techniques.

FIG. 6c shows a sketch of elliptical laminography, in which the major axis 11 of the ellipse runs horizontally. The reference point 8 is in the centre of the elliptical path 13. In elliptical laminography there is not only variation of the rotation angle α by the rotation 9, as shown in FIG. 6b and FIGS. 2 and 4 for rotational laminography, but there is also—which is not shown in FIG. 6c for reasons of clarity—variation of the tilt angle φ as a function of the rotation angle α. The relevant relation for the case shown of a horizontal major axis 11 is:

$$\phi(\alpha) = \phi_0 - 2a^*(1 - \cos \alpha).$$

$\phi_0$ is a maximum tilt angle that the system assumes in the position on the major axis 11; "a" is a measure for the eccentricity of the ellipse from the range $[0°; \phi_0/2]$.

The difference between the elliptical laminography shown in FIG. 6d and that in FIG. 6c is that the major axis 11 in FIG. 6d is not horizontal, but is at a constant torsional angle $\alpha_0$ to the horizontal. The resultant relation between the tilt angle φ and the rotation angle α is:

$$\phi(\alpha) = \phi_0 - 2a^*(1 - \cos(\alpha - \alpha_0)).$$

The difference between elliptical laminography and rotational laminography is essentially that in the former the depth resolution is not isotropic as in rotational laminography, but depends on the orientation of the major axis 11 and the relation between major axis and minor axis. The resultant relations for the depth resolution are known to a person skilled in the art, as they correspond to those that are also achieved by means of elliptical laminography known from the state of the art.

Apart from the laminography techniques already described (linear laminography according to FIG. 6a, rotational laminography according to FIG. 6b and elliptical laminography according to FIGS. 6c and 6d), with the method according to the invention it is also possible to provide a completely freely selectable distribution of the positions for feed-in of the first X-ray fluoroscopy images 1. This allows, for example, laminographic investigation of oversize testpieces or those that would not be accessible for other reasons, for example owing to unfavourable weight distribution, for testing with the symmetrically arranged positions described above. It should be noted that with completely freely selected positions, the depth resolution can vary from point to point within the test zone.

According to the invention, the positions at which the second X-ray fluoroscopy images 2 are fed in can also be freely selected. These X-ray fluoroscopy images are, through being reflected on a mirror plane that passes through the reference point 8 and is perpendicular to the central ray 4, sorted into the data set based on position.

In an advantageous embodiment, the reflections of the positions of the feed-in of the first X-ray fluoroscopy images 1, relative to the mirror plane that passes through the reference point 8 and is perpendicular to the central ray 4, are to be adopted as the positions at which the second X-ray fluoroscopy images 2 are fed in. By means of the industrial robot, it is then also possible to go to these positions without any problem, so that no part of the industrial robot is located in the beam path during feed-in both of the second X-ray fluoroscopy images 2 and of the first X-ray fluoroscopy images 1.

LIST OF REFERENCE SYMBOLS 1 first X-ray fluoroscopy images
2 second X-ray fluoroscopy images
3 X-ray tube
4 central ray
5 X-ray detector
6, 6' object
7, 7' normal
8 reference point
9 rotation
10 mirror motion
11 major axis
12 circular path
13 elliptical path
14 horizontal
15 motion
16 manipulator system
17 manipulator axis
$\alpha$ rotation angle
$\alpha_0$ constant torsional angle
$\phi, \phi'$ tilt angle
$\phi_0$ maximum tilt angle
a measure for the eccentricity

The invention claimed is:

1. A method for feeding-in X-ray fluoroscopy images in the context of a digital laminography technique, the method comprising:
   securing an object to be examined on a fixing device of a multiaxis manipulator system;
   positioning the object using the multiaxis manipulator system so that a central ray of an X-ray fluoroscopy device including an X-ray tube and an X-ray detector passes through a reference point to be defined;
   moving the object using the multiaxis manipulator system such that the reference point remains essentially unchanged relative to the X-ray irradiation device to obtain a first set of X-ray fluoroscopy images comprising the following steps:
   (a) tilting the object such that an axis through the reference point of the object, normal to a surface of the object forms a tilt angle ($\phi$) with the central ray between −45° and +45°,
   (b) rotating the object about the axis, while the tilt angle ($\phi$) remains unchanged, through a set of rotation angles ($\alpha$) located between −90° and +90°; and
   (c) feeding-in the X-ray fluoroscopy images obtained at each position corresponding to the set of rotation angles;
   moving the object using the multiaxis manipulator system such that the reference point remains essentially unchanged relative to the X-ray irradiation device to obtain a second set of X-ray fluoroscopy images by repeating steps (a)-(c), wherein the second set of images are obtained at a set of positions reflective of the first set of images relative to a mirror plane that passes through the reference point and is perpendicular to the central ray;
   reflecting the second set of X-ray fluoroscopy images, using an analysis unit, in the horizontal and vertical direction to create a set of reflected X-ray fluoroscopy images; and
   combining the first set of X-ray fluoroscopy images and the set of reflected X-ray fluoroscopy images to form a digital laminography data set.

2. The method according to claim 1, wherein the reference point is located in the object.

3. The method according to claim 1, wherein the tilt angle ($\phi$) is related to the rotation angle ($\alpha$) as follows:

$$\phi(\alpha)=\phi_0-2a^*(1-\cos(\alpha-\alpha_0)),$$

wherein $\phi_0$ is an assignable constant tilt angle from the range [0°; 90°] and $\alpha_0$ is an assignable constant torsional angle from the range [−90°; +90°] and "a" is an assignable measure for the eccentricity from the range [0; $\phi_0/2$].

4. The method according to claim 2, wherein the constant rotation angle is $\alpha_0=0°$.

5. The method according to claim 1, wherein the tilt angle ($\phi$) is constant.

6. The method according to claim 1, wherein the rotation angle ($\alpha$) is constant.

7. The method according to claim 1, wherein the set of rotation angles ($\alpha$) includes a first angle of −90° corresponding to one of the first set of images and includes a second angle of +90° corresponding to another one of the first set of images.

8. The method according to claim 1, wherein each of the first set of rotations angles ($\alpha$) during feed-in of the first X-ray fluoroscopy images have equal rotation angle distances from one another.

9. The method according to claim 8, wherein adjacent rotations angles of the first set of rotations angles ($\alpha$) are twisted relative to one another through a rotation angle $\alpha=10°$.

10. The method according to claim 1, wherein none of the parts of the multiaxis manipulator system is located in the beam path of the X-ray fluoroscopy device, neither in positions corresponding to the set of rotation angles nor in the set of positions reflective of the first set of images.

* * * * *